US012558320B2

(12) United States Patent
Guha et al.

(10) Patent No.: US 12,558,320 B2
(45) Date of Patent: *Feb. 24, 2026

(54) METHOD OF PREPARING A SOLID DOSAGE FORM AND A LUBRICANT

(71) Applicant: Evonik Operations GmbH, Essen (DE)

(72) Inventors: Ashish Guha, Mumbai (IN); Vinay Jain, Mumbai (IN); Shraddha Joshi, Thane (IN); Theresia Kuntz, Frankfurt (DE); Christian Mahlmeister, Ginsheim-Gustavsburg (DE); Jean-Luc Herbeaux, Cascais (PT)

(73) Assignee: Evonik Operations GmbH, Essen (DE)

( * ) Notice: Subject to any disclaimer, the term of this patent is extended or adjusted under 35 U.S.C. 154(b) by 964 days.

This patent is subject to a terminal disclaimer.

(21) Appl. No.: 17/633,434

(22) PCT Filed: Aug. 7, 2020

(86) PCT No.: PCT/EP2020/072212
§ 371 (c)(1),
(2) Date: Feb. 7, 2022

(87) PCT Pub. No.: WO2021/023848

PCT Pub. Date: Feb. 11, 2021

(65) Prior Publication Data
US 2022/0287979 A1 Sep. 15, 2022

(30) Foreign Application Priority Data

Aug. 8, 2019 (IN) .............................. 201941032091
Oct. 10, 2019 (EP) ..................................... 19202419

(51) Int. Cl.
| | |
|---|---|
| *A61K 9/20* | (2006.01) |
| *A61K 9/16* | (2006.01) |
| *A61K 31/55* | (2006.01) |
| *A61K 31/554* | (2006.01) |

(52) U.S. Cl.
CPC .......... *A61K 9/2095* (2013.01); *A61K 9/1694* (2013.01); *A61K 9/2013* (2013.01); *A61K 31/55* (2013.01); *A61K 31/554* (2013.01)

(58) Field of Classification Search
None
See application file for complete search history.

(56) References Cited

U.S. PATENT DOCUMENTS

| | | | |
|---|---|---|---|
| 2003/0215501 A1* | 11/2003 | Myatt | .................. A61P 3/06 424/738 |
| 2011/0236476 A1 | 9/2011 | Manku | |
| 2013/0095178 A1 | 4/2013 | Manku | |
| 2014/0274987 A1 | 9/2014 | Mccarty | |
| 2016/0120796 A1 | 5/2016 | Mccarty | |
| 2019/0083403 A1* | 3/2019 | Djordjevic | ......... A61K 31/4045 |
| 2019/0201364 A1 | 7/2019 | Manku | |

FOREIGN PATENT DOCUMENTS

| | | | |
|---|---|---|---|
| WO | WO 2010/028067 A1 | 3/2010 | |
| WO | WO-2016102316 A1 * | 6/2016 | ............... A23D 7/00 |
| WO | WO-2019008101 A1 * | 1/2019 | ........... A61K 31/202 |
| WO | WO-2019034698 A1 * | 2/2019 | ........... A23L 33/115 |

OTHER PUBLICATIONS

International Search Report and Written Opinion issued on Oct. 9, 2020 in PCT/EP2020/072212 filed on Aug. 7, 2020, 15 pages.
Extended European Search Report issued on Apr. 6, 2020 in European Patent Application No. 19202419.8 filed on Oct. 10, 2019, 8 pages.
Yamamoto et al., "Lubricant and Bactericidal Properties of Calcium Salts of Fatty Acids: Effect of Degree of Unsaturation", Journal of Oleo Science, 2015, vol. 64, No. 10, pp. 1095-1100.
U.S. Appl. No. 17/633,434, filed Feb. 7, 2022, Ashish Guha, et al.
U.S. Appl. No. 17/633,462, filed Feb. 7, 2022, Ashish Guha, et al.
European Office Action issued Aug. 29, 2023 in European Application 20751154.4, 5 pages.

* cited by examiner

*Primary Examiner* — Susan T Tran
(74) *Attorney, Agent, or Firm* — Oblon, McClelland, Maier & Neustadt, L.L.P.

(57) ABSTRACT

The present invention is related to a method of preparing a solid dosage form, comprising the steps of: a. preparing a lubricant consisting of at least one polyunsaturated fatty acid salt; b. adding the lubricant and ingredients for the solid dosage form to a mixer; c. optionally carrying out one or more of the following steps: granulation, drying and sizing, d. blending the contents of the mixer; and e. compressing or slugging the blended contents to produce a solid dosage form. Solid dosage forms prepared according to this method and the use of PUFA salts as lubricant in tableting applications for compression of solid components are further comprised by the present invention.

17 Claims, 2 Drawing Sheets

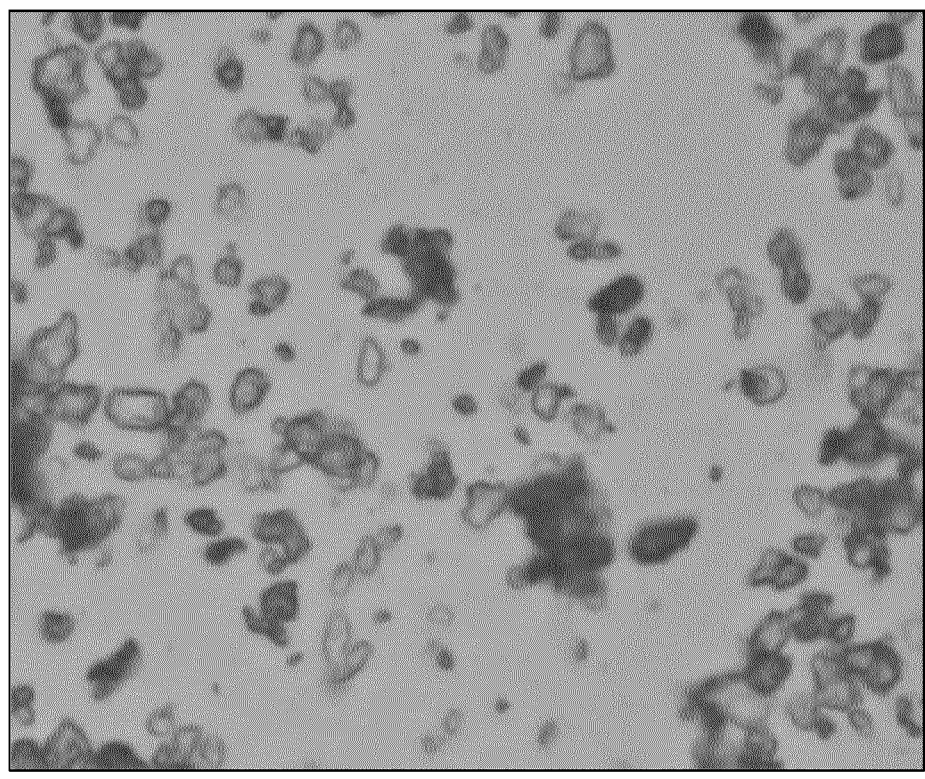
Fig. 1: Calcium salt of C18:0 fatty acid particles at 40X magnification
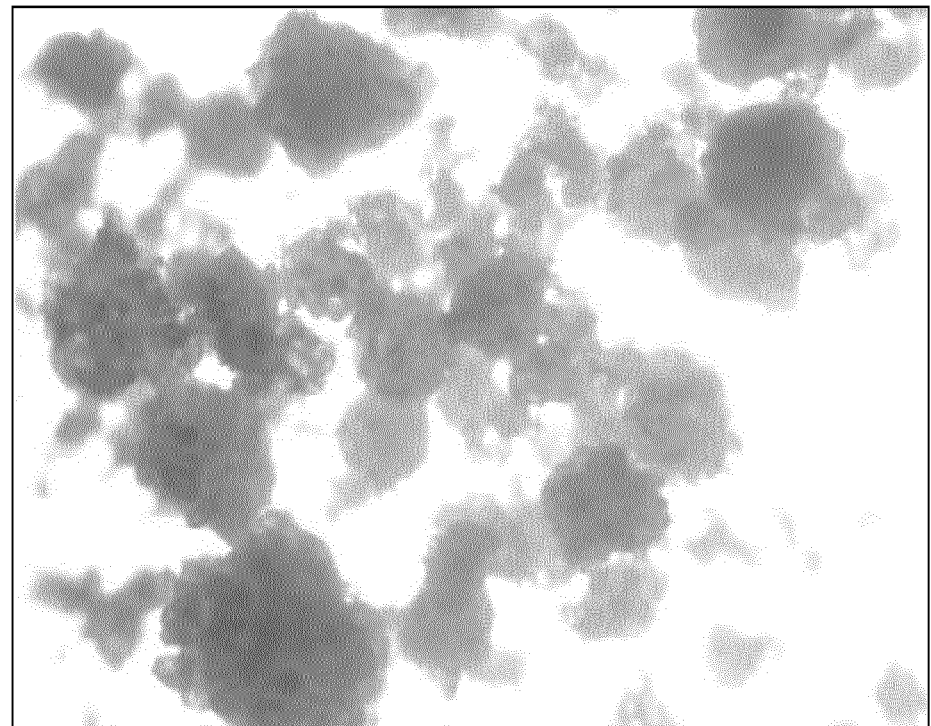
Fig. 2: Omega-3 lysine salt particles at 4X magnification

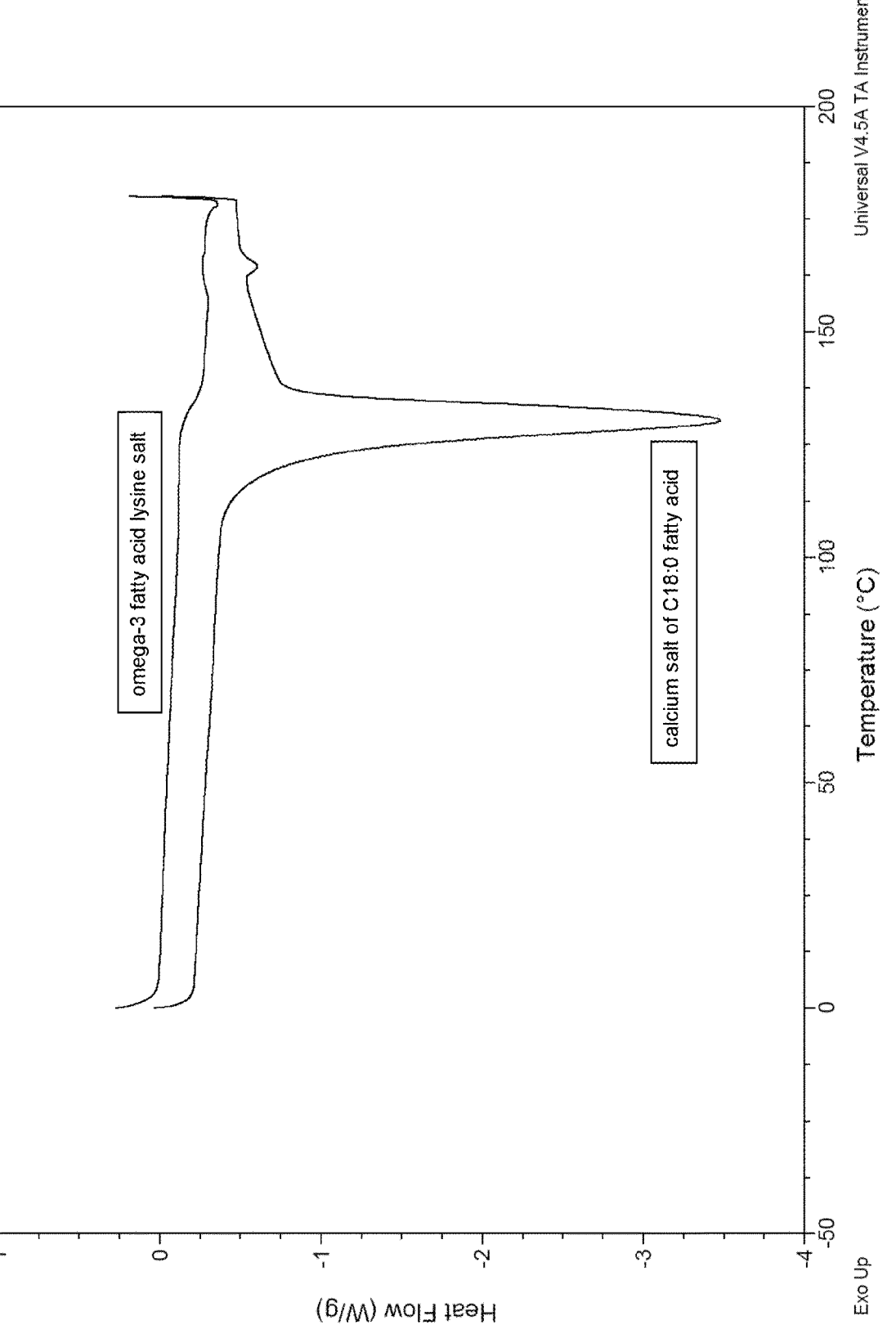
Fig. 3: DSC thermogram of omega-3 fatty acid lysine salt and calcium salt of C18:0 fatty acid

METHOD OF PREPARING A SOLID DOSAGE FORM AND A LUBRICANT

The present invention is related to a method of preparing a solid dosage form, comprising the steps of: a. preparing a lubricant consisting of at least one polyunsaturated fatty acid (PUFA) salt; b. adding the lubricant and ingredients for the solid dosage form to a mixer; c. optionally carrying out one or more of the following steps: granulation, drying and sizing, d. blending the contents of the mixer; and e. compressing or slugging the blended contents to produce a solid dosage form. Solid dosage forms prepared according to this method and the use of PUFA salts as lubricant in tableting applications for compression of solid components are further comprised by the present invention.

The invention provides alternate formulations for nutraceutical and pharmaceutical tablets, which are free from magnesium stearate and without need of adding any other known lubricants, thereby avoiding all the problems associated with them.

Lubrication plays a key role in successful manufacturing of pharmaceutical solid dosage forms; lubricants are essential ingredients in robust formulations to achieve this. Although many failures in pharmaceutical manufacturing operations are caused by issues related to lubrication, in general, lubricants do not gain adequate attention in the development of pharmaceutical formulations.

For pharmaceutical operations such as blending, roller compaction, tablet manufacturing, and capsule-filling, lubrication is essential in order to reduce the friction between the surfaces of manufacturing equipment and that of organic solids as well as to ensure the continuation of an operation (Wang, J. et al., Eur. J. Pharm. Biopharm. 2010, 75, 1-15). Pharmaceutical lubricants are agents added to tablet and capsule formulations in a very small quantity (usually 0.25%-5.0%, w/w) to improve the powder processing properties of formulations. Although a fairly small amount, lubricants play important roles in manufacturing; they decrease friction at the interface between a tablet's surface and the die wall during ejection so that the wear on punches and dies is reduced; they prevent sticking of tablets to punch faces as well as sticking of capsules to dosators and tamping pins. In terms of powder flow, lubricants can improve the flowability of blends and aid unit operations (Li and Wu, lubricants 2014, 2: 21-43).

Most of the lubricants used in the pharmaceutical processes are metallic salts of fatty acids. Magnesium stearate, calcium stearate, zinc stearate as well as stearic acid are the most common ones. Magnesium stearate is the most frequently used lubricant. However, there are several problems associated with the use of stearic acid and its metallic salts like magnesium stearate and calcium stearate as a lubricant including undesirable delayed dissolution of actives, degradation of and interactions with certain classes of drugs, including the amines and ACE inhibitors.

In a recent study, the mechanism underlying the delay in drug release caused by magnesium stearate was investigated with model metformin hydrochloride (HCl) tablets containing magnesium stearate by using the stationary disk method, scanning electron microscopy with energy dispersive X-ray spectrometry (SEM-EDS), and Fourier transform infrared spectroscopy (FTIR). The results revealed the process and mechanism of delay: the exposed amount of magnesium stearate on the tablet surface increases during the dissolution process, and tablet dissolution is limited by the diffusion of magnesium stearate (Ariyasu et al., Int J Pharm 2016, 511 (2): 757-64).

Moreover, several adverse health effects are associated with the use of stearic acid, palmitic acid and saturated fats, including effects on cardiovascular health, ocular health, and the immune system. Most of the commonly used lubricants (such as stearic acid and it's derivatives, hydrogenated vegetable oil and glyceryl behanate) contain one or more of harmful constituents mentioned above or get converted metabolically into stearic acid in-vivo as in case of sodium stearyl fumarate.

Problem: Magnesium stearate is a common lubricant used for solid pharmaceutical formulations and is known for its property to cause delay of tablet dissolution and affecting tablet strength adversely in higher concentrations. As described in the prior art section, most of the commonly used lubricants have quality issues, or pose adverse health challenges, including that on cardiovascular health. Prolonged use of these lubricants like for example in health supplements is not desirable as the health risks can multiply many folds.

Thus, there is a need to develop nutraceutical and pharmaceutical formulations free of commonly used lubricants such as stearic acid, magnesium and calcium stearate, hydrogenated vegetable oil, sodium stearyl fumarate, glyceryl behenate and talc.

WO 2008/130883 A highlights the importance and requirement of finding new tablet lubricants and describes use of oily liquid embedded in insoluble matrix as a lubricant for tablets. The matrix with embedded lubrication comprises an oily liquid finely dispersed in an oil insoluble material. In an exemplary embodiment the nutritional supplement composition is substantially free of stearate. Oily liquids suitable for dispersion in the oil insoluble material include vitamin E, preferably in the form of vitamin E acetate, animal oil, synthetic oil, mineral oil, polyethylene glycol, silicon oil and combinations thereof. Suitable oil insoluble materials include starch, dextrin, microcrystalline cellulose, ethylcellulose, gelatin, sugars, glucose, maltose, fructose, sorbitol, sucrose, mannitol, sorbitol, lactose, methylcellulose, hydroxypropylmethyl cellulose, maltodextrin, silicon dioxide, anhydrous dicalcium phosphate, and combinations thereof.

Solution: It was surprisingly found that use of salts of polyunsaturated fatty acids as lubricant in tablet formulations yields very good tableting behavior with wide variety of pharmaceutical and nutraceutical ingredients and that the disintegration/dissolution of these tablets is not significantly delayed even at high concentrations.

It was also found that it is preferable to use amino acid or magnesium ($Mg^{2+}$) or potassium ($K^+$) salts of polyunsaturated fatty acids as lubricant in absence of magnesium stearate in order to obtain a superior product.

The invention provides a one-step solution to most of the problems associated with the use of existing tableting lubricants including quality, processing and health issues.

The present invention is related to a method of preparing a solid dosage form, comprising the steps of:
  a. preparing a lubricant consisting of at least one polyunsaturated fatty acid salt;
  b. adding the lubricant and ingredients for the solid dosage form to a mixer;
  c. optionally carrying out one or more of the following steps: granulation, drying and sizing,
  d. blending the contents of the mixer;
  e. compressing or slugging the blended contents to produce a solid dosage form.

With this method solid dosage forms can easily be prepared which are suitable for direct compression and without the need of further known lubricants, such as magnesium stearate, due to the surprising lubricant effect of the polyunsaturated fatty acid salts.

In capsule filling operation, the powder is filled into capsules usually after forming a slug in both, dosator and tamping based capsule filling machines. Similarly, in order to produce granules of higher density and flow, the powder is compressed between the two rollers or punches to form slugs, which are further broken down into smaller particles and processed further into different dosage forms. Both Those processes are referred to as slugging according to the present invention.

Numerous health benefits have been correlated with the supplemental intake of polyunsaturated fatty acids (PUFAs) by an extensive body of evidence gathered over the course of the past several decades. Prevention of cardiovascular disease and reducing the symptoms of inflammatory conditions are amongst the most prominent examples, however, preventing the promotion and progression stages of some types of cancer, reducing blood pressure and blood cholesterol as well as positive effects in the treatment of depression and schizophrenia, Alzheimer's disease, dyslexia, and attention-deficit or hyperactivity disorder, amongst others, have been reported as well. Furthermore, because some PUFAs are considered to be essential for the development of brain, nervous system and eye, nowadays routinely, infant nutrition is supplemented with specific PUFAs.

In the context of the present invention the term PUFA is used interchangeably with the term polyunsaturated fatty acid and defined as follows: Fatty acids are classified based on the length and saturation characteristics of the carbon chain. Short chain fatty acids have 2 to about 6 carbons and are typically saturated. Medium chain fatty acids have from about 6 to about 14 carbons and are also typically saturated. Long chain fatty acids have from 16 to 24 or more carbons and may be saturated or unsaturated. In longer chain fatty acids there may be one or more points of unsaturation, giving rise to the terms "monounsaturated" and "polyunsaturated," respectively. In the context of the present invention long chain polyunsaturated fatty acids having 20 or more carbon atoms are designated as polyunsaturated fatty acids or PUFAs.

PUFAs are categorized according to the number and position of double bonds in the fatty acids according to well established nomenclature. There are two main series or families of LC-PUFAs, depending on the position of the double bond closest to the methyl end of the fatty acid: The omega-3 series contains a double bond at the third carbon, while the omega-6 series has no double bond until the sixth carbon. Thus, docosahexaenoic acid (DHA) has a chain length of 22 carbons with 6 double bonds beginning with the third carbon from the methyl end and is designated "22:6 n-3" (all-cis-4,7,10,13,16,19-docosahexaenoic acid). Another important omega-3 PUFA is eicosapentaenoic acid (EPA) which is designated "20:5 n-3" (all-cis-5,8,11,14,17-eicosapentaenoic acid). An important omega-6 PUFA is arachidonic acid (ARA) which is designated "20:4 n-6" (all-cis-5,8,11,14-eicosatetraenoic acid).

Other omega-3 PUFAs include: Eicosatrienoic acid (ETE) 20:3 (n-3) (all-cis-11,14,17-eicosatrienoic acid), Eicosatetraenoic acid (ETA) 20:4 (n-3) (all-cis-8,11,14,17-eicosatetraenoic acid), Heneicosapentaenoic acid (HPA) 21:5 (n-3) (all-cis-6,9,12,15,18-heneicosapentaenoic acid), Docosapentaenoic acid (Clupanodonic acid) (DPA) 22:5 (n-3) (all-cis-7,10,13,16,19-docosapentaenoic acid), Tetracosapentaenoic acid 24:5 (n-3) (all-cis-9,12,15,18,21- tetracosapentaenoic acid), Tetracosahexaenoic acid (Nisinic acid) 24:6 (n-3) (all-cis-6,9,12,15,18,21-tetracosahexaenoic acid).

Other omega-6 PUFAs include: Eicosadienoic acid 20:2 (n-6) (all-cis-11,14-eicosadienoic acid), Dihomo-gamma-linolenic acid (DGLA) 20:3 (n-6) (all-cis-8,11,14-eicosatrienoic acid), Docosadienoic acid 22:2 (n-6) (all-cis-13,16-docosadienoic acid), Adrenic acid 22:4 (n-6) (all-cis-7,10, 13,16-docosatetraenoic acid), Docosapentaenoic acid (Osbond acid) 22:5 (n-6) (all-cis-4,7,10,13,16-docosapentaenoic acid), Tetracosatetraenoic acid 24:4 (n-6) (all-cis-9, 12,15,18-tetracosatetraenoic acid), Tetracosapentaenoic acid 24:5 (n-6) (all-cis-6,9,12,15,18-tetracosapentaenoic acid).

Preferred omega-3 PUFAs used in the embodiments of the present invention are docosahexaenoic acid (DHA) and eicosapentaenoic acid (EPA).

In a preferred configuration of the present invention, the polyunsaturated fatty acid salt comprises at least one basic amino acid or at least counter ion selected from magnesium ($Mg^{2+}$) and potassium ($K^+$). In a further preferred configuration, the omega-3 or omega-6 fatty acid salts have an organic counter ion selected from lysine, arginine, ornithine, choline and mixtures of the same.

The basic amino acids are preferably selected from lysine, arginine, ornithine and mixtures of the same.

The present invention is especially suitable for solid dosage form, which can be tablets, where the blended contents are compressed in a tableting machine.

Tablet compression leads to the consolidation of particles into a pellet of specific strength. Tablet compression normally results in particle rearrangement, deformation of particles, interparticulate bond formation, and elastic recovery upon ejection of the compact from the die. The penultimate step in a tablet compression process is ejection. The ejection force is the force needed to push the tablet out of the die. Significant decrease in the overall ejection force is observed when the material and/or the die are properly lubricated. The extent of lubrication also becomes important in the last step during tablet compression when the tablet leaves the lower punch. Lubrication is most relevant to the tablet ejection and tablet take-off steps as the lubricant helps to reduce the friction between the tablet and the metal surface, making the overall tablet compression process much smoother.

It has been observed that a powder with acceptable tableting performance on a small-scale operation may become problematic with longer running time or upon scaling up, leading to high ejection forces, high wear & tear of the tooling and even overloading of the machine leading to stopping of the process. Clearly, a reliable prediction of changes in compaction and ejection properties via lab trials is practically important.

Therefore, in a preferred embodiment of the present invention, when the solid dosage form is a tablet, the blended contents are compressed in a tableting machine and the ejection force of the tableting machine is not more than 150N, preferably not more than 130N, more preferably not more than 120N, most preferably between 50N and 120N.

It is particularly preferred when the mean particle size of the lubricant before mixing is between 2 μm and 600 μm.

In an advantageous configuration of the present invention, the lubricant is prepared by admixing aqueous, aqueous-alcoholic or alcoholic solutions of a composition comprising at least one polyunsaturated omega-3 fatty acid or omega-6 fatty acid component and a composition containing a basic organic acid selected from lysine, arginine, ornithine, choline or at least counter ion selected from magnesium ($Mg^{2+}$) and potassium ($K^+$) and mixtures of the same, and subjecting resulting admixture to spray drying conditions or an extruder-based process subsequently, thus forming a solid product composition comprising at least one salt of a cation derived from the basic amino acid or magnesium ($Mg^{2+}$) or potassium ($K^+$) with an anion derived from a polyunsaturated omega-3 fatty acid or omega-6 fatty acid.

Recently, a technology has been described to stabilize EPA/DHA free fatty acids with amino acids resulting in solid and somewhat inert salts of EPA/DHA that can be introduced into e.g. food or supplement preparations. WO2016102323A1 describes compositions comprising polyunsaturated omega-3 fatty acid salts that can be stabilized against oxidation.

Compositions comprising polyunsaturated fatty acids that can be stabilized against oxidation may be obtained from any suitable source material which, additionally, may have been processed by any suitable method of processing such source material. Typical source materials include any part of fish carcass, vegetables and other plants as well as material derived from microbial and/or algal fermentation. Typically, such material further contains substantial amounts of other naturally occurring fatty acids. Typical methods of processing such source materials may include steps for obtaining crude oils such as extraction and separation of the source material, as well as steps for refining crude oils such as settling and degumming, de-acidification, bleaching, and deodorization, and further steps for producing PUFA-concentrates from refined oils such as de-acidification, transesterification, concentration, and deodorization (cf. e.g. EFSA Scientific Opinion on Fish oil for Human Consumption). Any processing of source materials may further include steps for at least partially transforming PUFA-esters into the corresponding free PUFAs or inorganic salts thereof.

Preferred compositions comprising PUFAs that can be stabilized against oxidation by the process of the present invention can be obtained from compositions mainly consisting of esters PUFAs and other naturally occurring fatty acids by cleavage of the ester bonds and subsequent removal of the alcohols previously bound as esters. Preferably, ester cleavage is performed under basic conditions. Methods for ester cleavage are well known in the art.

According to the present invention, the spray drying conditions comprise a pure spray drying or a spray granulation process, or continuous spray granulation.

A solid dosage form prepared according to the present invention is a further subject of the present invention. The solid dosage form may be a tablet or capsule and preferably has extended release, immediate release or delayed release characteristics.

In a preferred embodiment, the amount of polyunsaturated fatty acid salt in the solid dosage form is 50 weight-% or less, preferably 40 weight-% or less, more preferably between 0.5 and 30 weight-%.

Salts of lysine with polyunsaturated fatty acids per se are known in the art (cf. EP 0734373 B1), and were described as "very thick transparent oils, which transform into solids of waxy appearance and consistency at low temperatures" (cf. EP 0734373 B1, page 1, lines 47 to 48). However, salts of PUFAs can be obtained via spray drying conditions as described in WO2016102323A1 and WO2016102316A1.

In a preferred embodiment of the present invention, the amount of polyunsaturated fatty acid is 65 weight % or less, preferably 60 weight % or less, more preferably between 40 and 55 weight-% with respect to the total weight of polyunsaturated fatty acid salt.

The solid dosage form according to the present invention comprises one or more active pharmaceutical or nutraceutical ingredients and one or more excipients, and wherein the excipients are preferably selected from the group of binders, antioxidants, glidants, lubricants, pigments, plasticizers, polymers, brighteners, diluents, flavors, surfactants, pore formers, stabilizers or any combinations thereof.

In a preferred embodiment, the composition has a glass transition temperature Tg between 120° C. and 180° C., determined using differential scanning calorimetry (DSC).

Since several adverse health effects are associated with the use of stearic acid, palmitic acid and saturated fats, including effects on cardiovascular health, ocular health, and the immune system, it is desirable to reduce to a minimum the amount of magnesium stearate in solid dosage forms. Therefore, in a preferred embodiment, the solid dosage form comprises less than 0.5 weight-%, preferably less than 0.2 weight-%, more preferably between 0 and 0.1 weight-% magnesium stearate, or no magnesium stearate at all.

In a preferred embodiment, the solid dosage form is an immediate release tablet and the disintegration time in water is not more than 30 min. Preferably, the disintegration time in water is not more than 20 min, more preferably not more than 15 min, most preferably not more than 10 min.

It is preferred when in the solid dosage form, the polyunsaturated fatty acid salt comprises at least one basic amino acid or at least counter ion selected from magnesium ($Mg^{2+}$) and potassium ($K^+$). In a further preferred configuration, the omega-3 fatty acid salts have an organic counter ion selected from lysine, arginine, ornithine, choline and mixtures of the same.

The basic amino acids are preferably selected from lysine, arginine, ornithine and mixtures of the same.

The present invention is also directed to a preparation comprising at least one polyunsaturated fatty acid salt comprising at least one omega-3 or omega-6 fatty acid salt selected from eicosapentaenoic acid (EPA), docosahexaenoic acid (DHA), arachidonic acid (ARA), alpha linolenic acid, stearidonic acid, eicosatetraenoic acid, docosapentaenoic acid, linoleic acid, γ-linolenic acid for use as lubricant in tableting applications for compression of solid components.

In a preferred configuration, the omega-3 fatty acid component is selected from EPA or DHA. In a further preferred configuration, the omega-3 or omega-6 fatty acid salt has an organic counter ion selected from lysine, arginine, ornithine, choline or magnesium ($Mg^{2+}$), potassium ($K^+$) and mixtures of the same.

In a preferred embodiment, the amount of polyunsaturated fatty acid is 65 weight % or less, preferably 60 weight % or less, more preferably between 40 and 55 weight-% with respect to the total weight of polyunsaturated fatty acid salt.

In a preferred embodiment, the amount of polyunsaturated fatty acid salt in the tableting composition is 50 weight-% or less, preferably 40 weight-% or less, more preferably between 0.5 and 30 weight-%.

WORKING EXAMPLES

Polyunsaturated Fatty Acid Compositions

In the examples for the present invention, different polyunsaturated fatty acid compositions were used. Different omega-3 fatty acid salts having an organic counter ion selected from the basic amino acids lysine, arginine and ornithine were prepared. The omega-3 fatty acids Eicosapentaenoic acid (C20:5w3c) (EPA) and Docosahexaenoic acid (C22:6w3c) (DHA) are present in a ratio of around 2:1 (ratio EPA:DHA). The salts were prepared by spray granulation as described in WO2016102323A1.

The omega-3 lysine salt (omega-3-lys) contains around 32 weight-% of L-lysine and around 65 weight-% of polyunsaturated fatty acids (AvailOm®, Evonik Nutrition and Care GmbH, Germany). The major polyunsaturated fatty acids in the composition are the omega-3 fatty acids Eicosapentaenoic acid (C20:5w3c) (EPA) and Docosahexaenoic acid (C22:6w3c) (DHA), summing up to around 58 weight-% of the composition. The composition also contains minor amounts of Docosaenoic acid isomer (incl. erucic acid) (C22:1), Docosapentaenoic acid (C22:5w3c) and of the omega-6 fatty acids Arachidonic acid (C20:4w6) and Docosatetraenoic acid (C22:4w6c).

The omega-3 arginine salt (omega-3-arg) contains around 35 weight-% of L-arginine and around 64 weight-% of polyunsaturated fatty acids. The major polyunsaturated fatty acids in the composition are the omega-3 fatty acids Eicosapentaenoic acid (C20:5w3c) (EPA) and Docosahexaenoic acid (C22:6w3c) (DHA), summing up to around 49 weight-% of the composition. The composition alsocontains minor amounts of Docosaenoic acid isomer (incl. erucic acid) (C22:1), Docosapentaenoic acid (C22:5w3c) and of the omega-6 fatty acids Arachidonic acid (C20:4w6) and Docosatetraenoic acid (C22:4w6c).

The omega-3 ornithine salt (omega-3-orn) contains around 29 weight-% of L-ornithine and around 70 weight-% of polyunsaturated fatty acids. The major polyunsaturated fatty acids in the composition are the omega-3 fatty acids Eicosapentaenoic acid (C20:5w3c) (EPA) and Docosahexaenoic acid (C22:6w3c) (DHA), summing up to around 54 weight-% of the composition. The composition also contains minor amounts of Docosaenoic acid isomer (incl. erucic acid) (C22:1), Docosapentaenoic acid (C22:5w3c) and of the omega-6 fatty acids Arachidonic acid (C20:4w6) and Docosatetraenoic acid (C22:4w6c).

Salts of $K^+$ and mixed salts of $K^+$ and lysine (50:50) and mixed salts of ornithine and lysine (50:50) were prepared by spray granulation as described in WO2016102323A1 using the PUFA composition described above. The $Mg^{2+}$ salts and mixed salts of $Mg^{2+}$ and lysine (50:50) were prepared by kneading as described in WO2017202935A1 using the PUFA composition described above.

Examples 1-6 (Comparative): Effect of Commonly Used Lubricants on Disintegration of Benazepril Tablets Benazepril HCl was used as a prototype drug using commonly used lubricants in their recommended range, such as magnesium stearate (2-3%) and Lubritab (5-10%). Benazepril tablets were prepared by direct compression. galenIQ 721 was passed through 20 # sieve, Benazepril HCl was passed through 60 # sieve and lubricants (magnesium stearate or Lubritab) were passed through a 80 # sieve. Benazepril and galenIQ 721 were mixed together for 10 min. After that, required amount of lubricant was added and mixed for 1 minute (*in some batches mixing time was 5 minutes after addition of lubricant). Compression of prepared blend was carried out at average tablet weight of 200 mg using 8 mm circular biconvex punch (tablet formulations are shown in table 1).

TABLE 1

| Formulation for Benazepril tablets, amount of ingredients is given in % w/w | | | | | | |
|---|---|---|---|---|---|---|
| | Example | | | | | |
| | C-1 | C-2 | C-3 | C-4 | C-5 | C-6 |
| Benazepril HCl | 10 | 10 | 10 | 10 | 10 | 10 |
| galenIQ 721 | 88 | 88 | 87 | 87 | 85 | 80 |
| Magnesium stearate | 2 | 2 | 3 | 3 | — | — |
| Lubritab | — | — | — | — | 5 | 10 |
| Total | 100 | 100 | 100 | 100 | 100 | 100 |
| Mixing time (min) * | 1 | 5 | 1 | 5 | 1 | 1 |

Concentration and mixing time of commonly used lubricants have a negative impact on the disintegration time on tablets. Disintegration time increased with increase in mixing time and increase in the concentration of the lubricant magnesium stearate (table 2).

TABLE 2

| Results for tableting trials | | | | | | |
|---|---|---|---|---|---|---|
| | Example | | | | | |
| | C-1 | C-2 | C-3 | C-4 | C-5 | C-6 |
| Lubricant concentration in tablet (% w/w) | 2 | 2 | 3 | 3 | 5 | 10 |
| Mixing time for lubricant (min) | 1 | 5 | 1 | 5 | 1 | 1 |
| Compression force (kN) | 5.0-6.0 | 5.0-6.0 | 5.0-6.0 | 5.0-6.0 | 5.0-7.0 | 6.0-10.0 |
| Ejection force (N) | 105-106 | 105-106 | 106-107 | 105-106 | 105-106 | 112-114 |
| Tablet thickness (mm) | 3.83-3.87 | 3.83-3.85 | 3.83-3.86 | 3.83-3.84 | 3.80-3.86 | 4.0-4.1 |
| Hardness (N) | 100-120 | 90-110 | 90-110 | 80-90 | 90-110 | 100-120 |
| Disintegration time water (min) | 27 | 65 | >120 | >120 | 16 | 37 |

Example 7 (Comparative): Quantification of Stearic Acid and Palmitic Acid Content Metallic salts of fatty acids are commonly used as lubricants in the pharmaceutical industry, where magnesium stearate, calcium stearate, and zinc stearate are the three common metallic salts of fatty acids. Magnesium stearate is the most frequently used, however, when used in combination with omega-3 fatty acid salts leads to an increase of concentrations of stearic acid and palmitic acid in solution. This effect was analyzed in detail.

For the quantification of stearic acid and palmitic acid in water from magnesium stearate alone 1 mg magnesium stearate was added in water under high shear homogenization and mixed for 15 min under continuous homogenization. After homogenization, the prepared dispersion was centrifuged to remove bigger particle size. The supernatant solution was then filtered through 0.2-micron nylon syringe filter and the filtrate was analyzed for content of stearic acid and palmitic acid.

For the quantification of stearic acid and palmitic acid in water from magnesium stearate in combination with omega-3 fatty acid salts, 1 g magnesium stearate and 10 g omega-3 fatty acid lysine salt (omega-3-lys) was added in water under high shear homogenization and mixed for 15 min under continuous homogenization. After homogenization, the prepared dispersion was centrifuged to remove bigger particle size. The supernatant solution was then filtered through 0.45 $\mu$m (B1) or 0.2 $\mu$m (B2) nylon syringe filter and the filtrate were analyzed for content of stearic acid and palmitic acid. The results are shown in table 3.

TABLE 3

Quantification of stearic acid and palmitic acid in mixtures with
omega-3 fatty acid salts, amount of ingredients is given in % w/w

| Example | Condition | Stearic acid | Palmitic acid | Total fatty acid in media (%) |
|---|---|---|---|---|
| Magnesium stearate | 0.2 $\mu$m filtered | 0.00 | 2.91 | 2.91 |
| Omega-3-lys + Mg. stearate (10:1) | 0.2 $\mu$m filtered | 6.59 | 6.72 | 13.32 |
| Omega-3-lys + Mg. stearate (10:1) | 0.45 $\mu$m filtered | 6.61 | 8.24 | 14.86 |

TABLE 3-continued

Quantification of stearic acid and palmitic acid in mixtures with
omega-3 fatty acid salts, amount of ingredients is given in % w/w

| Example | Condition | Stearic acid | Palmitic acid | Total fatty acid in media (%) |
|---|---|---|---|---|
| Magnesium stearate powder | unfiltered | 50.64 | 49.35 | — |

Examples 1-6 (Inventive): Effect of Omega-3 Amino Acid Salts on Disintegration of Benazepril Tablets Benazepril HCl was used as a prototype drug using omega-3 lysine salt as a lubricant in the range of 2-10%. Benazepril tablets were prepared by direct compression. galenIQ 721 was passed through a 20 # sieve, Benazepril HCl was passed through a 60 # sieve and omega-3 lysine salt was passed through a 80 # sieve. Benazepril and galenIQ 721 were mixed and subsequently the omega-3 lysine salt was added and mixed for 1 minute (*in some batches mixing time was 5 minutes or 10 minutes after addition of lubricant). Compression of prepared blend was carried out at average tablet weight of 200 mg using 8 mm circular biconvex punch (tablet formulations are shown in table 4).

TABLE 4

Formulation for Benazepril tablets, amount of
ingredients is given in % w/w

| | Example | | | | | |
|---|---|---|---|---|---|---|
| | I-1 | I-2 | I-3 | I-4 | I-5 | I-6 |
| Benazepril HCl | 10 | 10 | 10 | 10 | 10 | 10 |
| galenIQ 721 | 88 | 88 | 87 | 87 | 85 | 80 |
| Omega-3 lysine salt | 2 | 2 | 3 | 3 | 5 | 10 |
| Total | 100 | 100 | 100 | 100 | 100 | 100 |
| Mixing time* | 1 | 5 | 1 | 5 | 1 | 1 |

TABLE 5

Results for tableting trials

| | Example | | | | | |
|---|---|---|---|---|---|---|
| | I-1 | I-2 | I-3 | I-4 | I-5 | I-6 |
| Lubricant concentration in tablet (% w/w) | 2 | 2 | 3 | 3 | 5 | 10 |
| Mixing time for lubricant (min) | 1 | 5 | 1 | 5 | 1 | 1 |
| Punch size (mm) | 8 | 8 | 8 | 8 | 8 | 8 |
| Average weight (mg) | 200 | 200 | 200 | 200 | 200 | 200 |
| Compression force (kN) | 5.0-6.0 | 5.0-6.0 | 5.0-6.0 | 5.0-6.0 | 5.0-7.0 | 6.0-10.0 |
| Ejection force (N) | 105-106 | 105-106 | 105-106 | 105-106 | 105-106 | 112-114 |
| Tablet thickness (mm) | 3.80-3.86 | 3.80-3.86 | 3.80-3.86 | 3.80-3.86 | 3.80-3.86 | 3.80-3.9 |
| Hardness (N) | 90-110 | 90-110 | 90-110 | 90-110 | 90-110 | 90-110 |
| Disintegration time water (min) | 8 | 8 | 8 | 8 | 9 | 11 |

Concentration and mixing time of omega-3 lysine salt did not show any negative impact on the disintegration time of tablets as shown in table 5. Disintegration time did not increase with increase in mixing time and increase in the omega-3 lysine salt in the tablets. For a mixing time of 10 min instead of 5 min, the same values for disintegration time in water (8 min) were obtained.

Examples 7-13 (Inventive): Effect of Omega-3 Amino Acid Salts on Disintegration of Diltiazem Tablets All tablets were prepared by direct compression. All excipients were passed through a 20 # sieve and Diltiazem HCl was passed through a 60 # sieve and the ingredients were mixed for 5 min (table 6). Compression of prepared blend was then carried out using single rotary tablet compression machine.

While optimal ejection force is achieved with as low as 0.5% w/w concentration of omega-3 fatty acid salt in tablets, the disintegration time remains below 30 minutes up to ~50% w/w concentration.

Examples 14-18 (Inventive): Salts of Omega 3 Fatty Acids as a Lubricant with Different Type of Excipients and APIs All tablets were prepared by direct compression. The excipients were passed through a 20 # sieve, the APIs were passed through a 60 # sieve and omega-3 fatty acid salts were passed through 100 # sieve. All ingredients except omega-3 lysine or arginine salts were mixed for 10 min, the

TABLE 6

Formulation for Diltiazem tablets, amount of ingredients is given in % w/w

| | Example | | | | | | | |
| | Comp. | I-7 | I-8 | I-9 | I-10 | I-11 | I-12 | I-13 |
|---|---|---|---|---|---|---|---|---|
| Diltiazem HCl | 5.45 | 5.45 | 5.45 | 5.45 | 5.45 | 5.45 | 5.45 | 5.45 |
| galenIQ 721 | 94.55 | 94.05 | 89.55 | 84.55 | 74.55 | 64.55 | 44.55 | 34.55 |
| Omega-3 lysine salt | 0 | 0.5 | 5 | 10 | 20 | 30 | 50 | 60 |
| Total | 100 | 100 | 100 | 100 | 100 | 100 | 100 | 100 |
| Mixing time | 5 | 5 | 5 | 5 | 5 | 5 | 5 | 5 |

Tableting trials were performed with the compositions from table 5 with raising lubricant concentrations, punch size was 11 mm, average weight was 550 mg, the compression force was 5.0-7.0 kN for all trials.

omega-3 salt was added subsequently and mixed for 1 minute. Compression of prepared blend as shown in table 8 was then carried out using single rotary tablet compression machine.

TABLE 7

Results for tableting trials

| | Example | | | | | | | |
| | Comp. | I-7 | I-8 | I-9 | I-10 | I-11 | I-12 | I-13 |
|---|---|---|---|---|---|---|---|---|
| Lubricant concentration in tablet (% w/w) | 0 | 0.5 | 5 | 10 | 20 | 30 | 50 | 60 |
| Ejection force (N) | 99-210 | 95-99 | 95-97 | 95-97 | 95-97 | 100-103 | 95-97 | 100-103 |
| Tablet thickness (mm) | NA | 6.1-6.2 | 6.1-6.2 | 6.1-6.2 | 6.1-6.2 | 6.2-6.3 | 6.2-6.3 | 6.2-6.3 |
| Hardness (N) | NA | 110-120 | 70-90 | 80-100 | 100-110 | 80-100 | 100-110 | 80-100 |
| Disintegration time water (min) | NA | 3 | 5 | 8 | 16 | 16 | 23 | 39 |

In the comparative example, no tablets were formed. Sticking to the die wall was observed and the tablet broke into two parts after compression. Moreover, ejection force increased drastically (111 N from initial) after 1 minute of compression and further tableting was not possible. While using omega-3 lysine salt as a lubricant, ejection force increase remains below 5 N with maximum ejection force of just 103 N and the disintegration time was acceptable. The results are summarized in table 7.

TABLE 8

Formulation for tablets, amount of ingredients is given in % w/w

| | Example | | | | | |
| | Comp. | I-14 | I-15 | I-16 | I-17 | I-18 |
|---|---|---|---|---|---|---|
| galenIQ 721 | 100 | 95 | — | — | — | — |
| Omega-3 lysine salt | 0 | 5 | 1 | 0.5 | 1 | — |
| Omega-3 arginine salt | — | — | — | — | — | 1 |

TABLE 8-continued

Formulation for tablets, amount of ingredients is given in % w/w

| | Example | | | | |
| | Comp. | I-14 | I-15 | I-16 | I-17 | I-18 |
|---|---|---|---|---|---|---|
| Theophylline | — | — | 39.6 | 39.6 | — | 33.33 |
| SuperTab 24 AN (Lactose) | — | — | 54.4 | 54.9 | — | 60.67 |
| Paracetamol granules | — | — | — | — | 82.34 | — |
| Sodium starch glycolate | — | — | 5 | 5 | 2.91 | 5 |
| Microcrystalline cellulose | — | — | — | — | 13.65 | — |
| Total | 100 | 100 | 100 | 100 | 100 | 100 |

TABLE 9

Results for tableting trials

| | Example | | | | |
| | Comp. | I-14 | I-15 | I-16 | I-17 | I-18 |
|---|---|---|---|---|---|---|
| Lubricant concentration in tablet (% w/w) | 0 | 5 | 1 | 0.5 | 1 | 1 |
| Punch size (mm) | 12 | 12 | 9 | 9 | 8 | 9 |
| Average Weight (mg) | 550 | 550 | 300 | 300 | 200 | 300 |
| Ejection force (N) | 114-204 | 107-113 | 93-94 | 93-94 | 95-97 | 91-94 |
| Disintegration time water (min) | 4 | 7 | 3 | 3 | 6 | 6 |

Ejection force increased in absence of any lubricant in the formulation (comp. example). There was an increase by 90 N in the ejection force from initial within 5 minutes of run time and further processing was not possible. Although a tablet was formed in the comparative example, the tableting machine will stop after a few tablets due to the increase in ejection force.

The ejection force did not increase during compression of tablets when omega-3 lysine or arginine salts were used as lubricant in all tablet formulations. Moreover, the disintegration time in water was below 10 min with different types of excipients and APIs with different solubility. The results are summarized in table 9.

Examples 19-24 (Inventive): Different Salts of Omega 3 Fatty Acids as a Lubricant with Diltiazem Tablets Different omega-3 fatty acid salts were used as lubricant, such as magnesium salt of EPA and DHA (Mg salt), potassium salt of EPA and DHA (K salt), ornithine salt of EPA and DHA and mixtures of magnesium and lysine salt of EPA and DHA (50% magnesium salt and 50% lysine salt), mixtures of potassium and lysine salt of EPA and DHA (50% potassium salt and 50% lysine salt) and mixtures of ornithine salt and lysine salt of EPA and DHA (50% ornithine salt and 50% lysine salt).

All tablets were prepared by direct compression. The excipients were passed through a 20 # ASTM sieve, the APIs were passed through a 60 # ASTM sieve and omega-3 fatty acid salts were mixed with Galen IQ 721 in a mixer grinder and then passed through 40 # ASTM sieve. All ingredients were mixed together for 5 min. Compression of prepared blend as shown in table 10 was then carried out using single rotary tablet compression machine, punch size was 11 mm, average weight was 550 mg, the compression force was 5.0-8.0 kN for all trials.

TABLE 10

Formulation for Diltiazem tablets, amount of ingredients is given in % w/w

| | Example | | | | | |
| | Comp. | I-19 | I-20 | I-21 | I-22 | I-23 | I-24 |
|---|---|---|---|---|---|---|---|
| Diltiazem HCl | 5.45 | 5.45 | 5.45 | 5.45 | 5.45 | 5.45 | 5.45 |
| galenIQ 721 | 94.55 | 89.55 | 89.55 | 89.55 | 89.55 | 89.55 | 89.55 |
| Omega-3 Mg salt | — | 5 | — | — | — | — | — |
| Omega-3 Mg + lysine salt | — | — | 5 | — | — | — | — |
| Omega-3 K + lysine salt | — | — | — | 5 | — | — | — |
| Omega-3 orn. + lysine salt | — | — | — | — | 5 | — | — |
| Omega-3 K salt | — | — | — | — | — | 5 | — |
| Omega-3 ornithine salt | — | — | — | — | — | — | 5 |
| Total | 100 | 100 | 100 | 100 | 100 | 100 | 100 |

TABLE 11

Results for tableting trials

| | Example | | | | | |
| | Comp. | I-19 | I-20 | I-21 | I-22 | I-23 | I-24 |
|---|---|---|---|---|---|---|---|
| Lubricant conc. in tablet (% w/w) | 0 | 5 | 5 | 5 | 5 | 5 | 5 |
| Ejection force (N) | 99-210 | 108-110 | 108-120 | 110-111 | 110-115 | 111-114 | 111-114 |
| Tablet thickness (mm) | NA | 6.0-6.1 | 6.0-6.1 | 5.9-6.0 | 5.9-6.0 | 5.9-6.0 | 5.9-6.0 |
| Hardness (N) | NA | 120-140 | 100-130 | 45-60 | 75-100 | 115-140 | 115-140 |

TABLE 11-continued

| | | | Results for tableting trials | | | |
|---|---|---|---|---|---|---|
| | | | | Example | | |
| | Comp. | I-19 | I-20 | I-21 | I-22 | I-23 | I-24 |
| Disintegration time water (min) | NA | 3-5 | 3-5 | 6-8 | 6-7 | 9-10 | 9-10 |

In the comparative example, no tablets were formed. Sticking to the die wall was observed and the tablet broke into two parts after compression. Moreover, ejection force increased drastically (increase by 111 N as compared to initial) after 1 minute of compression and further tableting was not possible.

While using different types of omega-3 salts as a lubricant, ejection force increase remains below 12 N with maximum ejection force of just 120 N and the disintegration time was acceptable. The results are summarized in table 11.

Examples 25 (Inventive): Microscopic Analysis of Omega-3 Fatty Acid Lysine Salt in Comparison to Calcium Salt of C18:0 Fatty Acid (Calcium Stearate)

Small amounts of calcium salt of C18:0 fatty acid or omega-3 fatty acid lysine salt was placed on a glass slide followed by spreading it over the slide uniformly. The prepared slides were mounted on a digital microscope equipped with camera (Zeiss) and particles were then focused at different magnifications such as 4×, 10× and 40×. Microscopic images were capture at magnification where particles shape visible clearly. FIG. 1 shows calcium salt of C18:0 fatty acid particles at 40× magnification and FIG. 2. shows omega-3 lysine salt particles at 4× magnification.

Microscopy of calcium salt of C18:0 fatty acid (calcium stearate) shows very fine particles agglomerates and irregular plates-lamellar layers like structures (visible at 40× magnification). As reported in literature (e.g. "Yamamoto T et al, Lubricant and Bactericidal properties of calcium salts of fatty acids: Effect of degree of unsaturation, Journal of Oleo Science 64, (10) 1095-1100, 2015"), the lubricant effect of calcium salt of C18:0 fatty acid is due to cleavage of lamellar layers and disintegration of powder agglomerates. This disruption in the structural system allows for absorption of friction force between solids surfaces. In addition to this, due to the hydrophobic nature of the calcium salt of C18:0 fatty acid, adhesion properties between particles decrease and result in lubrication effect.

In contrast, microscopy of omega-3 fatty acid lysine salt shows bigger particles, having spheroidal shape (visible at 4× magnification). Contrary to the calcium salt of C18:0 fatty acid, the omega-3 fatty acid lysine salt is water soluble, hydrophilic and has a different particle morphology. Results suggest that the lubricant effect of omega-3 salts according to the present invention is new and independent of particle size morphology and hydrophobic nature as reported in literature for the calcium salt of C18:0 fatty acid.

Examples 26 (Inventive): Differential Scanning Calorimetry (DSC) Analysis of Omega-3 Fatty Acid Lysine Salt in Comparison to Calcium Salt of C18:0 Fatty Acid (Calcium Stearate)

Samples of omega-3 fatty acid lysine salt and calcium salt of C18:0 fatty acid (5-10 mg) were placed in an aluminum pan crimped with hermatic lid and heated from 0 to 180° C. at a rate of 10° C. per min using a DSC (TA Instruments, USA, Model-Q20). Nitrogen was used as purge gas at a flux rate of 50 ml per min. The calibration of temperature and heat flow was performed with standard indium samples. FIG. 3 shows DSC thermogram of omega-3 fatty acid lysine salt and calcium salt of C18:0 fatty acid.

DSC analysis of calcium salt of C18:0 fatty acid (calcium stearate) shows a sharp melting peak at 130° C. Such a sharp melting peak is an indication of the crystalline nature of the material. The crystal structure of the calcium salt of C18:0 fatty acid is responsible for lubrication properties as reported in literature (e.g.—Yamamoto T et al, Lubricant and Bactericidal properties of calcium salts of fatty acids: Effect of degree of unsaturation, Journal of Oleo Science 64, (10) 1095-1100, 2015). Whereas in case of the omega-3 fatty acid lysine salt no sharp peak observed, which indicates an amorphous nature of the material, which was highlighted in literature as not being suitable for providing lubricant effect.

The invention claimed is:

1. A method of preparing a solid dosage form, the method comprising:
   a. preparing a lubricant comprising at least one polyunsaturated fatty acid salt;
   b. adding the lubricant and ingredients for the solid dosage form to a mixer;
   c. optionally carrying out-granulation, drying, and/or sizing,
   d. blending the contents of the mixer; and
   e. compressing or slugging the blended contents to produce the solid dosage form;
   wherein the at least one polyunsaturated fatty acid salt comprises omega-3 fatty acids EPA and/or DHA; and
   wherein the composition has a glass transition temperature Tg between 120° C. and 180° C., determined using differential scanning calorimetry (DSC).

2. The method according to claim 1, wherein when the solid dosage form is a tablet, the blended contents are compressed in a tableting machine and ejection force of the tableting machine is not more than 150N.

3. The method according to claim 1, wherein the at least one polyunsaturated fatty acid salt comprises omega-3 fatty acids EPA and DHA.

4. The method according to claim 1, wherein the at least one polyunsaturated fatty acid salt comprises at least one basic amino acid or at least counter ion selected from the group consisting of magnesium ($Mg^{2+}$) and potassium ($K^+$).

5. The method according to claim 1, wherein a mean particle size of the lubricant before the adding is between 2 µm and 600 µm.

6. The method according to claim 1, wherein the lubricant is prepared by
   admixing aqueous, aqueous-alcoholic or alcoholic solutions of a composition comprising at least one polyunsaturated omega-3 fatty acid or omega-6 fatty acid component and a composition comprising: a basic amino acid selected from lysine, arginine, or ornithine; choline; or at least a counter ion selected from the group consisting of magnesium ($Mg^{2+}$) and potassium ($K^+$) and mixtures of the same, and subjecting resulting admixture to spray drying conditions or an extruder-based process subsequently, thus forming a solid product composition comprising at least one salt of a cation derived from the basic amino acid or magnesium ($Mg^{2+}$) or potassium ($K^+$) with an anion derived from a polyunsaturated omega-3 fatty acid or omega-6 fatty acid.

7. The method according to claim 6, wherein the spray drying conditions comprise a pure spray drying or a spray granulation process or continuous spray granulation.

8. A solid dosage form prepared according to claim 1.

9. The solid dosage form according to claim 8, wherein the solid dosage form is a tablet or capsule.

10. The solid dosage form according to claim 8, wherein an amount of polyunsaturated fatty acid salt in the solid dosage form is 50 weight-% or less.

11. The solid dosage form according to claim 8, wherein an amount of polyunsaturated fatty acid is 65 weight % or less with respect to a total weight of polyunsaturated fatty acid salt.

12. The solid dosage form according to claim 8 wherein the ingredients of the dosage form comprise one or more active pharmaceutical or nutraceutical ingredients and one or more excipients, and wherein the excipients are at least one selected from the group consisting of binders, antioxidants, glidants, lubricants, pigments, plasticizers, polymers, brighteners, diluents, flavors, surfactants, pore formers, and stabilizers.

13. The solid dosage form according to claim 8, wherein the solid dosage form comprises less than 0.5 weight-magnesium stearate or no magnesium stearate at all.

14. The solid dosage form according to claim 8, wherein the solid dosage form is an immediate release tablet and has a disintegration time in water of not more than 30 min.

15. A preparation, comprising at least one polyunsaturated fatty acid salt comprising at least one omega-3 or omega-6 fatty acid salt selected from the group consisting of eicosapentaenoic acid (EPA), docosahexaenoic acid (DHA), arachidonic acid (ARA), alpha linolenic acid, stearidonic acid, eicosatetraenoic acid, docosapentaenoic acid, linoleic acid, and γ-linolenic acid, for use as a lubricant in tableting applications for compression of solid components.

16. The preparation according to claim 15, wherein the omega-3 fatty acid component is selected from the group consisting of EPA and DHA.

17. The preparation according to claim 13, wherein the omega-3 or omega-6 fatty acid salt has a counter ion selected from the group consisting of lysine, arginine, ornithine, choline, magnesium ($Mg^{2+}$), potassium ($K^+$), and mixtures of the same.

* * * * *